(12) United States Patent
Gordon et al.

(10) Patent No.: US 7,316,708 B2
(45) Date of Patent: Jan. 8, 2008

(54) MEDICAL DEVICE DELIVERY SYSTEM

(75) Inventors: Lucas S. Gordon, Sammamish, WA (US); Mark L. Mathis, Kirkland, WA (US); Greg Nieminen, Bothell, WA (US)

(73) Assignee: Cardiac Dimensions, Inc., Kirkland, WA (US)

( * ) Notice: Subject to any disclaimer, the term of this patent is extended or adjusted under 35 U.S.C. 154(b) by 432 days.

(21) Appl. No.: 10/313,914

(22) Filed: Dec. 5, 2002

(65) Prior Publication Data

US 2004/0111095 A1 Jun. 10, 2004

(51) Int. Cl.
*A61F 2/06* (2006.01)
(52) U.S. Cl. ..................................... 623/1.11
(58) Field of Classification Search ............... 606/108, 606/191–198; 623/1.1, 1.11
See application file for complete search history.

(56) References Cited

U.S. PATENT DOCUMENTS

| | | | |
|---|---|---|---|
| 3,995,623 A | 12/1976 | Blake et al. |
| 4,055,861 A | 11/1977 | Carpentier et al. |
| 4,164,046 A | 8/1979 | Cooley |
| 4,485,816 A | 12/1984 | Krumme |
| 4,550,870 A | 11/1985 | Krumme et al. |
| 4,588,395 A | 5/1986 | Lemelson |
| 4,830,023 A | 5/1989 | de Toledo et al. |
| 5,061,277 A | 10/1991 | Carpentier et al. |
| 5,250,071 A | 10/1993 | Palermo |
| 5,261,916 A | 11/1993 | Engelson |
| 5,265,601 A | 11/1993 | Mehra |
| 5,350,420 A | 9/1994 | Cosgrove et al. |
| 5,441,515 A | 8/1995 | Khosravi et al. |
| 5,474,557 A | 12/1995 | Mai |
| 5,514,161 A | 5/1996 | Limousin |
| 5,554,177 A | 9/1996 | Kieval et al. |
| 5,562,698 A | 10/1996 | Parker |
| 5,584,867 A | 12/1996 | Limousin et al. |
| 5,601,600 A | 2/1997 | Ton |
| 5,676,671 A | 10/1997 | Inoue |
| 5,733,325 A | 3/1998 | Robinson et al. |
| 5,824,071 A | 10/1998 | Nelson et al. |
| 5,891,193 A | 4/1999 | Robinson et al. |
| 5,895,391 A | 4/1999 | Farnholtz |

(Continued)

FOREIGN PATENT DOCUMENTS

EP 0893133 A1 1/1999

(Continued)

OTHER PUBLICATIONS

Papageorgiou, P., et al., "Coronary Sinus Pacing Prevents Induction of Atrial Fibrillation," Circulation 96: 1893-1898, Sep. 16, 1977.

(Continued)

*Primary Examiner*—Kevin T. Truong
(74) *Attorney, Agent, or Firm*—Shay Glenn LLP

(57) ABSTRACT

A system for selectively deploying a medical device includes a cartridge that is engageable with a proximal end of a delivery catheter that is routed to a desired location in a patient's body. An advancement mechanism is provided for advancing the medical device out of the cartridge and into the delivery catheter for deploying the medical device at the desired location in the patient's body.

22 Claims, 5 Drawing Sheets

U.S. PATENT DOCUMENTS

| | | |
|---|---|---|
| 5,899,882 A | 5/1999 | Waksman et al. |
| 5,908,404 A | 6/1999 | Elliott |
| 5,928,258 A | 7/1999 | Khan et al. |
| 5,935,161 A | 8/1999 | Robinson et al. |
| 5,961,545 A | 10/1999 | Lentz et al. |
| 5,978,705 A | 11/1999 | KenKnight et al. |
| 5,984,944 A | 11/1999 | Forber |
| 6,015,402 A | 1/2000 | Sahota |
| 6,027,517 A | 2/2000 | Crocker et al. |
| 6,077,295 A | 6/2000 | Limon et al. |
| 6,077,297 A | 6/2000 | Robinson et al. |
| 6,096,064 A | 8/2000 | Routh |
| 6,099,549 A | 8/2000 | Bosma et al. |
| 6,099,552 A | 8/2000 | Adams |
| 6,129,755 A | 10/2000 | Mathis et al. |
| 6,171,320 B1 | 1/2001 | Monassevitch |
| 6,190,406 B1 | 2/2001 | Duerig et al. |
| 6,210,432 B1 | 4/2001 | Solem et al. |
| 6,254,628 B1 * | 7/2001 | Wallace et al. ............ 623/1.12 |
| 6,275,730 B1 | 8/2001 | KenKnight et al. |
| 6,342,067 B1 | 1/2002 | Mathis et al. |
| 6,345,198 B1 | 2/2002 | Mouchawar et al. |
| 6,352,553 B1 | 3/2002 | van der Burg et al. |
| 6,352,561 B1 | 3/2002 | Leopold et al. |
| 6,358,195 B1 | 3/2002 | Green et al. |
| 6,395,017 B1 | 5/2002 | Dwyer et al. |
| 6,402,781 B1 | 6/2002 | Langberg et al. |
| 6,419,696 B1 | 7/2002 | Ortiz et al. |
| 6,442,427 B1 | 8/2002 | Boute et al. |
| 6,503,271 B2 | 1/2003 | Duerig et al. |
| 6,537,314 B2 | 3/2003 | Langberg et al. |
| 6,569,198 B1 | 5/2003 | Wilson et al. |
| 6,589,208 B2 | 7/2003 | Ewers et al. |
| 6,602,288 B1 | 8/2003 | Cosgrove et al. |
| 6,602,289 B1 | 8/2003 | Colvin et al. |
| 6,623,521 B2 | 9/2003 | Steinke et al. |
| 6,626,899 B2 | 9/2003 | Houser et al. |
| 6,629,534 B1 | 10/2003 | St. Goar et al. |
| 6,629,994 B2 | 10/2003 | Gomez et al. |
| 6,643,546 B2 | 11/2003 | Mathis et al. |
| 6,656,221 B2 | 12/2003 | Taylor et al. |
| 6,709,425 B2 | 3/2004 | Gambale et al. |
| 6,716,158 B2 | 4/2004 | Raman et al. |
| 6,718,985 B2 | 4/2004 | Hlavka et al. |
| 6,723,038 B1 | 4/2004 | Schroeder et al. |
| 6,733,521 B2 | 5/2004 | Chobotov et al. |
| 6,764,510 B2 | 7/2004 | Vidlund et al. |
| 6,776,784 B2 | 8/2004 | Ginn |
| 6,790,231 B2 | 9/2004 | Liddicoat et al. |
| 6,793,673 B2 | 9/2004 | Kowalsky et al. |
| 6,960,229 B2 | 11/2005 | Mathis et al. |
| 6,966,926 B2 | 11/2005 | Mathis |
| 2001/0018611 A1 | 8/2001 | Solem et al. |
| 2001/0044568 A1 | 11/2001 | Langberg et al. |
| 2001/0049558 A1 | 12/2001 | Liddicoat et al. |
| 2002/0016628 A1 | 2/2002 | Langberg et al. |
| 2002/0035361 A1 | 3/2002 | Houser et al. |
| 2002/0042621 A1 | 4/2002 | Liddicoat et al. |
| 2002/0042651 A1 | 4/2002 | Liddicoat et al. |
| 2002/0049468 A1 | 4/2002 | Streeter et al. |
| 2002/0055774 A1 | 5/2002 | Liddicoat |
| 2002/0065554 A1 | 5/2002 | Streeter |
| 2002/0087173 A1 | 7/2002 | Alferness et al. |
| 2002/0095167 A1 | 7/2002 | Liddicoat et al. |
| 2002/0103532 A1 | 8/2002 | Langberg et al. |
| 2002/0103533 A1 | 8/2002 | Langberg et al. |
| 2002/0138044 A1 | 9/2002 | Streeter et al. |
| 2002/0151961 A1 | 10/2002 | Lashinski et al. |
| 2002/0169502 A1 | 11/2002 | Mathis |
| 2002/0169504 A1 | 11/2002 | Alferness et al. |
| 2002/0183835 A1 | 12/2002 | Taylor et al. |
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2003/0018358 A1 | 1/2003 | Saadat |
| 2003/0069636 A1 | 4/2003 | Solem et al. |
| 2003/0078465 A1 | 4/2003 | Pai et al. |
| 2003/0078654 A1 | 4/2003 | Taylor et al. |
| 2003/0083538 A1 | 5/2003 | Adams et al. |
| 2003/0083613 A1 | 5/2003 | Schaer |
| 2003/0088305 A1 | 5/2003 | Van Schie et al. |
| 2003/0105520 A1 | 6/2003 | Alferness et al. |
| 2003/0130730 A1 | 7/2003 | Cohn et al. |
| 2003/0130731 A1 | 7/2003 | Vidlund et al. |
| 2003/0135267 A1 | 7/2003 | Solem et al. |
| 2003/0144697 A1 | 7/2003 | Mathis et al. |
| 2003/0171776 A1 | 9/2003 | Adams et al. |
| 2003/0171806 A1 | 9/2003 | Mathis et al. |
| 2003/0212453 A1 | 11/2003 | Mathis et al. |
| 2003/0236569 A1 | 12/2003 | Mathis et al. |
| 2004/0010305 A1 | 1/2004 | Alferness et al. |
| 2004/0019377 A1 | 1/2004 | Taylor et al. |
| 2004/0039443 A1 | 2/2004 | Solem et al. |
| 2004/0073302 A1 | 4/2004 | Rourke et al. |
| 2004/0098116 A1 | 5/2004 | Callas et al. |
| 2004/0102839 A1 | 5/2004 | Cohn et al. |
| 2004/0111095 A1 | 6/2004 | Gordon et al. |
| 2004/0127982 A1 | 7/2004 | Machold et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0153147 A1 | 8/2004 | Mathis |
| 2004/0158321 A1 | 8/2004 | Reuter et al. |
| 2004/0176840 A1 | 9/2004 | Langberg |
| 2004/0193191 A1 | 9/2004 | Starksen et al. |
| 2004/0193260 A1 | 9/2004 | Alferness et al. |
| 2004/0220654 A1 | 11/2004 | Mathis |
| 2004/0220657 A1 | 11/2004 | Nieminen et al. |
| 2004/0243227 A1 | 12/2004 | Starksen et al. |
| 2004/0243228 A1 | 12/2004 | Kowalsky et al. |
| 2004/0249452 A1 | 12/2004 | Adams et al. |
| 2004/0260342 A1 | 12/2004 | Vargas et al. |
| 2005/0004667 A1 | 1/2005 | Swinford et al. |
| 2005/0010240 A1 | 1/2005 | Mathis et al. |
| 2005/0021121 A1 | 1/2005 | Reuter et al. |
| 2005/0027351 A1 | 2/2005 | Reuter et al. |
| 2005/0027353 A1 | 2/2005 | Alferness et al. |
| 2005/0033419 A1 | 2/2005 | Alferness et al. |
| 2005/0038507 A1 | 2/2005 | Alferness et al. |
| 2005/0065598 A1 | 3/2005 | Mathis et al. |
| 2005/0096666 A1 | 5/2005 | Gordon et al. |
| 2005/0119673 A1 | 6/2005 | Gordon et al. |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0137685 A1 | 6/2005 | Nieminen et al. |
| 2005/0149179 A1 | 7/2005 | Mathis et al. |
| 2005/0149180 A1 | 7/2005 | Mathis et al. |
| 2005/0149182 A1 | 7/2005 | Alferness et al. |
| 2005/0187619 A1 | 8/2005 | Mathis et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0209690 A1 | 9/2005 | Mathis et al. |
| 2005/0216077 A1 | 9/2005 | Mathis et al. |
| 2005/0261704 A1 | 11/2005 | Mathis |
| 2005/0272969 A1 | 12/2005 | Alferness et al. |
| 2006/0020335 A1 | 1/2006 | Kowalsky et al. |
| 2006/0030882 A1 | 2/2006 | Adams et al. |

| | | | |
|---|---|---|---|
| 2006/0116758 A1 | 6/2006 | Swinford et al. | |
| 2006/0142854 A1 | 6/2006 | Alferness et al. | |
| 2006/0161169 A1 | 7/2006 | Nieminen et al. | |
| 2006/0167544 A1 | 7/2006 | Nieminen et al. | |
| 2006/0173536 A1 | 8/2006 | Mathis et al. | |
| 2006/0191121 A1 | 8/2006 | Gordon | |

FOREIGN PATENT DOCUMENTS

| | | | |
|---|---|---|---|
| EP | 0903110 A1 | 3/1999 | |
| EP | 0968688 A1 | 1/2000 | |
| EP | 1050274 A1 | 11/2000 | |
| EP | 1095634 A2 | 5/2001 | |
| GB | 0741604 | 12/1955 | |
| WO | WO-98/56435 A1 | 12/1998 | |
| WO | WO 00/44313 A1 | 8/2000 | |
| WO | WO 00/60995 A2 | 10/2000 | |
| WO | WO-00/60995 A2 | 10/2000 | |
| WO | WO 00/74603 A1 | 12/2000 | |
| WO | WO 01/00111 A1 | 1/2001 | |
| WO | WO 01/50985 A1 | 7/2001 | |
| WO | WO-01/54618 A1 | 8/2001 | |
| WO | WO 01/87180 A2 | 11/2001 | |
| WO | WO-02/00099 A2 | 1/2002 | |
| WO | WO 02/01999 A2 | 1/2002 | |
| WO | WO 02/05888 A1 | 1/2002 | |
| WO | WO 02/19951 A1 | 3/2002 | |
| WO | WO 02/34118 A2 | 5/2002 | |
| WO | WO 02/47539 A2 | 6/2002 | |
| WO | WO 02/053206 A2 | 7/2002 | |
| WO | WO 02/060352 A1 | 8/2002 | |
| WO | WO 02/062263 A2 | 8/2002 | |
| WO | WO 02/062270 A1 | 8/2002 | |
| WO | WO 02/062408 A2 | 8/2002 | |
| WO | WO 02/076284 A2 | 10/2002 | |
| WO | WO 02/078576 A2 | 10/2002 | |
| WO | WO 02/096275 A2 | 12/2002 | |
| WO | WO-03/015611 A2 | 2/2003 | |
| WO | WO-03/049647 A1 | 6/2003 | |
| WO | WO-03/059198 A2 | 7/2003 | |
| WO | WO 03/063735 A2 | 8/2003 | |
| WO | WO 2004/045463 A2 | 6/2004 | |
| WO | WO2004/084746 | 10/2004 | |

OTHER PUBLICATIONS

Heartsite.com, Echocardiogram, 1999, p. 1-4, A.S.M. Systems Inc.

PCT Search Report (EPO), PCT/US03/37641 filed Nov. 25, 2003, Maling Date: Jul. 5, 2004.

Clifton Alferness, et al. U.S. Appl. No. 11/467,105 entitled "Device and method for modifying the shape of a body organ," filed Aug. 24, 2006.

Gregory Nieminen, et al. U.S. Appl. No. 11/458,040, entitled "MItral Valve Annuloplasty Device with Twisted Anchor," filed Jul. 17, 2006.

Gregory Nieminen, et al. U.S. Appl. No. 11/458,042, entitled "Mitral Valve Annuloplasty Device with Wide Anchor," filed Jul. 17, 2006.

Gray, H. Anatomy of the Human Body. The Systemic Veins. Philadelphia: Lea & Febiger, 1918; Bartleby.com. 2000. Available at www.bartleby.com/107/. Accessed Jun. 7, 2006.

Mark L. Mathis, et al. U.S. Appl. No. 11/279,352, entitled "Mitral Valve Annuloplasty Device with Vena Cava Anchor," filed Apr. 11, 2006.

* cited by examiner

MEDICAL DEVICE DELIVERY SYSTEM

FIELD OF THE INVENTION

The present invention relates to a medical devices in general, and in particular to systems for delivering medical devices through a catheter.

BACKGROUND OF THE INVENTION

In an effort to reduce patient trauma, shorten healing time, and reduce the risk of infection, many surgical procedures that previously required large incisions are now being performed using catheters and minimally invasive techniques. One area in which this is particularly true is in the field of vascular surgery. Medical devices such as ablation balloons or stents are often delivered to a desired location in a patient's body through a catheter that is inserted through a relatively small hole made in the patient's leg, neck or arm. The catheter is advanced through the vasculature to its intended destination and the medical device is then deployed from the catheter.

Some medical devices such as vascular stents are pre-packaged in a delivery catheter for use by a physician. However, such pre-loaded catheters are not always easy to route to their intended destination. If a pre-loaded catheter is to, be routed over a guidewire, there must be room for the guidewire to move past the medical device in a lumen of the catheter. Alternatively, a separate guidewire lumen must be provided. In either case the size of the catheter required is increased. In some cases, the pre-loaded catheter is advanced through a lumen of a guide catheter that has been previously placed at the intended destination. This approach requires that the guide catheter be made sufficiently large to accommodate the delivery catheter. However, to reduce patient complications, it is generally desirable to reduce the size of the catheters that are inserted into the patient.

Another problem that can occur during a minimally invasive surgical procedure is that the medical device becomes damaged prior to implantation. After the physician has placed a catheter in the desired location, the physician must insert the medical device into the end of the catheter that remains outside the patient. If the device is small and delicate, the physician may damage it while trying to fit it into the catheter and advance it to the desired location in the patient's body.

Finally, physicians generally want to be free to use the technique for placing a catheter that is best suited to the particular patient and the procedure to be performed. Physicians may not want to use the catheter in which a pre-loaded medical device is sold. For example, the physician may want to use a guide wire, dilator or steering catheter to direct the guide catheter tip into position to then guide the medical device into position.

Given these problems, there is a need for a mechanism that allows a medical device to be delivered to a desired location within a patient's body in a way that does not dictate a physician's choice of particular routing technique or require an increased catheter size and that reduces the risk of damage to the device.

SUMMARY OF THE INVENTION

The present invention is a system for delivering a medical device to an intended destination in a patient's body. A distal tip of a delivery catheter is routed by a physician to its intended destination. The delivery catheter can be routed via a number of techniques and may be selected by the physician for the particular procedure to be performed. A cartridge having a pre-loaded medical device is engaged with a proximal end of the delivery catheter and an advancement mechanism moves the pre-loaded medical device out of the cartridge and into the delivery catheter. The delivery catheter and medical device are then moved relatively with respect to each other to deploy the medical device at the intended destination in the patient's body. The medical device can be pushed to the distal end of the catheter. The advancing mechanism can then fix the medical device position while the catheter is withdrawn to deploy the device.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

As indicated above, the present invention is a mechanism for delivering a medical device or implant to a desired location within a patient's body, that does not require a physician to use a particular type of delivery catheter, or technique for placing the catheter. Furthermore, the present invention reduces the chance that a medical device will be damaged by the physician while inserting it into the catheter for delivery to its intended destination.

Figure 1:
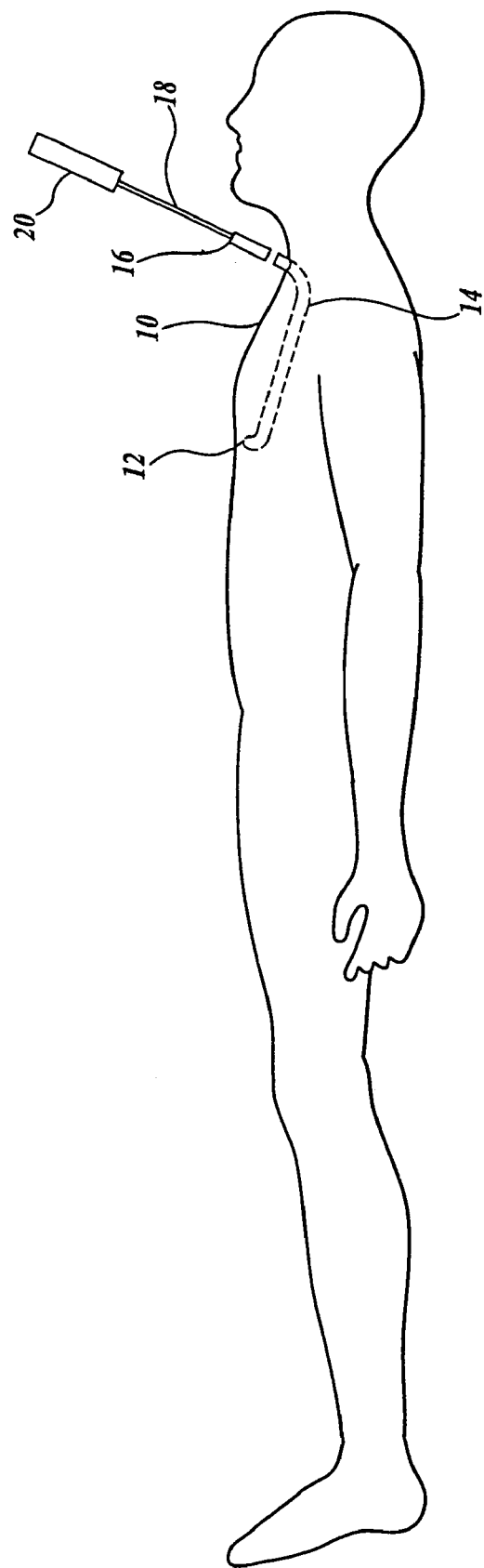
FIG. 1 illustrates a patient undergoing a minimally invasive procedure using a medical device delivery system in accordance with the present invention.

FIG. 1 illustrates a patient 10 undergoing a minimally invasive surgical procedure that requires a medical device to be delivered to a desired location 12 within the patient's body. To deliver the medical device, a physician routes a delivery catheter 14 through a small incision that is typically made in the patient's leg, neck or arm. The delivery catheter 14 is advanced through the vasculature until its distal end is positioned at or adjacent the desired location 12. Using the present invention, a physician is not limited to the type of delivery catheter that may be used or technique for routing it to the desired location. For example, the physician may use a steerable catheter, a guide catheter, a dilator or a catheter that is routed over a guidewire. Once the physician has routed the delivery catheter 14 to its desired location 12, the physician is ready to deliver a medical device to the desired location.

In accordance with the present invention, the medical device delivery system includes a cartridge 16 that can be engaged with a proximal end of the delivery catheter 14. The cartridge 16 holds a medical device within a lumen or cavity that is within the cartridge 16. The lumen in the cartridge that holds the medical device may have a constant diameter. Alternatively, the lumen may taper in either the proximal or distal direction.

With the cartridge 16 engaged with the delivery catheter 14, the medical device is aligned with a lumen of the delivery catheter 14. An advancement mechanism such as a push rod 18 is used by the physician to advance the medical device from within the cartridge 16 and through the delivery catheter 14 to its intended location. In one embodiment, the physician grasps a handle 20 at the proximal end of the push rod 18 and moves it towards the cartridge 16 in order to push the medical device out of the cartridge 16 through a connector that joins the cartridge 16 to the delivery catheter 14. The medical device may then be pushed out the distal end of the delivery catheter 14 at the desired location 12, or the medical device can be unsheathed by retracting the catheter. In some embodiments, the medical device is tethered to the advancement mechanism such that the medical device can be advanced from and retracted into the delivery catheter 14 if desired. In other embodiments, the medical device is not tethered such that once the medical device is advanced out of the distal end of the delivery catheter 14, it cannot be retrieved with the advancement mechanism.

Figure 2:
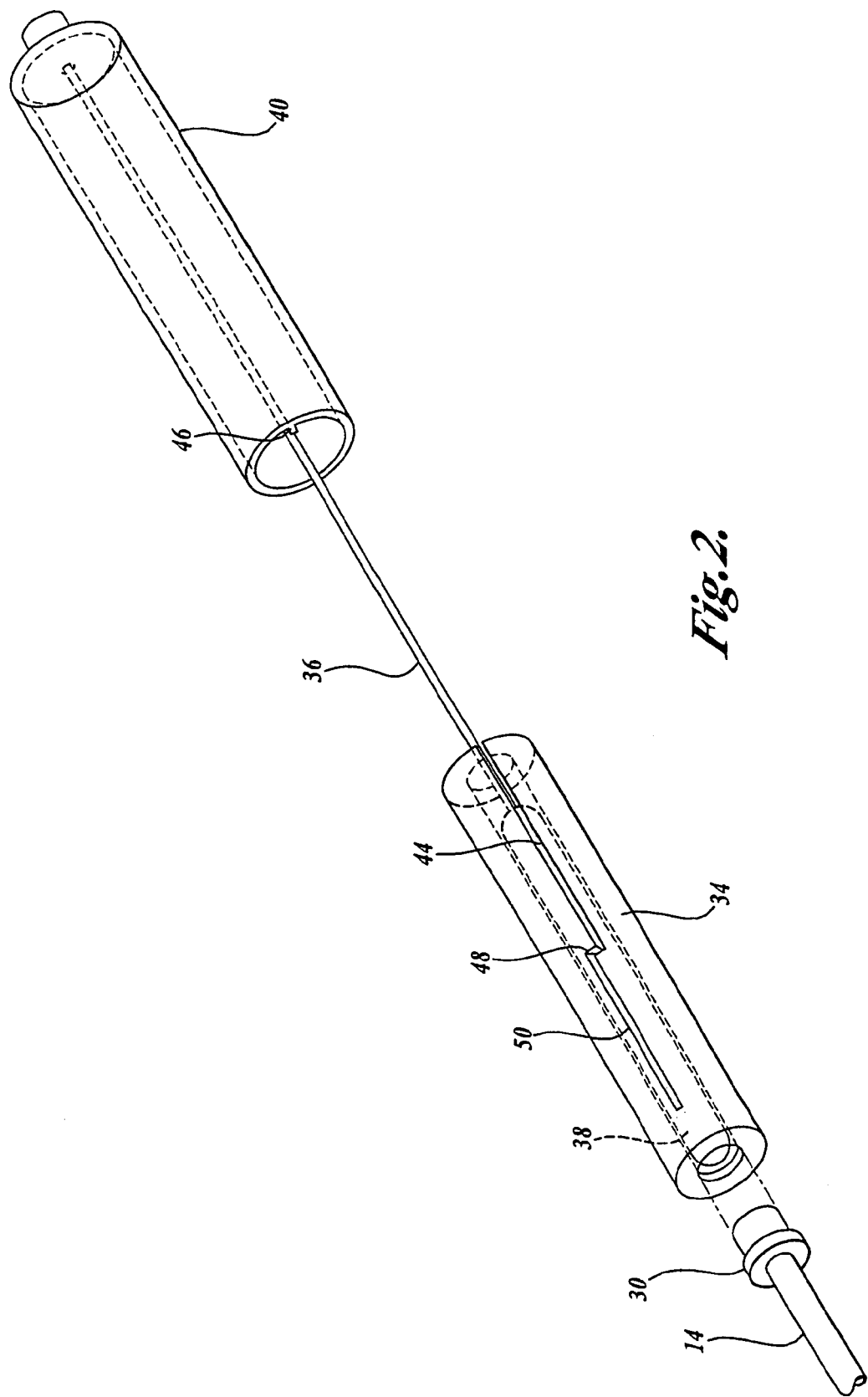
FIG. 2 illustrates a medical device delivery system in accordance with one embodiment of the present invention.

FIG. 2 illustrates one embodiment of a medical device delivery system in accordance with the present invention. A delivery catheter 14 has a connector 30 located at its proximal end that allows it to selectively engage a corresponding connector on the distal end of the cartridge 34 as described below. The connector 30 may be a luer fitting, a threaded connector, a quick release connector similar to those used on high pressure hoses, key and keyway or other device that allows the delivery catheter to become engaged with the distal end of the cartridge 34. The connector 30 has a lumen that aligns with a lumen or cavity in the cartridge 34 when the cartridge 34 is engaged with the connector 30. The delivery system also includes an advancement mechanism such as a push rod 36 that engages the medical device 38 within the cartridge 34. The proximal end of the push rod 36 is secured to a handle 40. The distal end of the push rod 36 is releasably connected to the medical device.

After engaging the distal end of the cartridge 34 and the proximal end of the delivery catheter 14, the physician pushes the handle 40 towards the cartridge 34 in order to move the medical device 38 out of the cartridge 34 and into a lumen of the delivery catheter 14. Further movement of the handle 40 with respect to the cartridge 34 advances the medical device 38 along the lumen of the delivery catheter 14 until it reaches the distal end of the delivery catheter 14. As will be appreciated, the distance that the medical device 38 can move depends upon the length of the push rod 36 compared to the length of the delivery catheter 14.

In some instances, it is desirable that the physician not be allowed to push the medical device 38 out the distal end of the catheter 14 without performing one or more required steps in a medical procedure. Therefore, mechanisms may be provided to limit the movement of the medical device in the delivery catheter until all required procedure steps have been completed. One such mechanism is shown in FIG. 2.

Here, a slot 44 is cut within the cartridge 34. The slot 44 extends from the distal end of the cartridge along its length until it reaches a stop 48. The slot 44 receives a tab 46 formed on an inner circumference of a lumen in the handle 40. When the tab 46 is aligned in the slot 44 of the cartridge, the cartridge 34 can be received into the lumen of the handle 40 until the tab 46 comes into contact with the stop 48. To further advance the handle over the cartridge, the handle 40 must be rotated with respect to the cartridge to move the slot around the circumference of the cartridge and align it with a second slot 50 that extends farther along the length of the cartridge. The stop 48 is positioned such that the medical device is at the correct position in the delivery catheter 14 for the physician to perform a desired procedure step. By providing one or more stops 48 and slots in the cartridge, the physician is less likely to fully advance the medical device within the delivery catheter 14 until all necessary steps in a procedure have been performed.

If the medical device 38 is coupled or tethered to the advancement mechanism, the medical device can be advanced or withdrawn in the delivery catheter 14 by moving the handle 40 towards or away from the cartridge 34.

Figure 3:
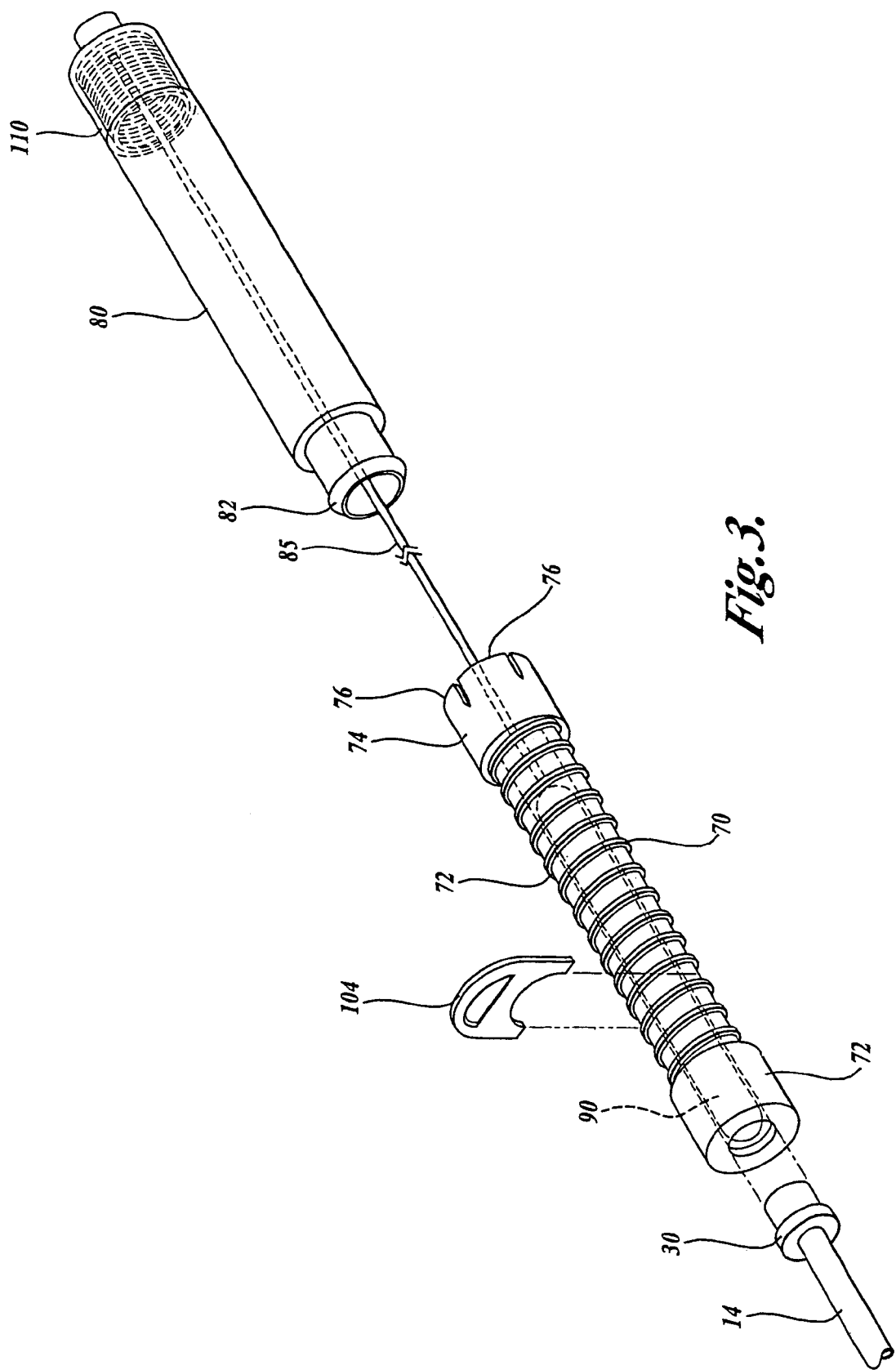
FIG. 3 illustrates another embodiment of a medical device delivery system in accordance with the present invention.

FIG. 3 illustrates another embodiment of a medical device delivery system in accordance with the present invention. As indicated above, a delivery catheter 14 has a connector 30 at its proximal end that allows the delivery catheter to be selectively engaged with a corresponding connector on a medical device delivery system. The medical device delivery system includes a cartridge 70 having a connector 72 at its distal end that engages the connector 30 in order to align a medical device 90 that is positioned within the cartridge 70 with a lumen of the delivery catheter 14.

On the outside of the cartridge 70 are a series of threads 72. A nut 74 on the cartridge can be rotated to advance the nut along the length of the threads 72. The nut 74 is designed to rotatably couple to a handle 80 that is secured to the proximal end of a push rod 85. In one embodiment, the distal end of the handle has a fitting 82 with a lip 84. When the handle 80 is engaged with the cartridge 70, leaves 76 on the nut 74 are forced over the lip 84 such that the nut 74 is rotatably coupled to the handle 80. The handle 80 has an interior lumen that is large enough to accommodate the cartridge. When the nut 74 is rotated, the cartridge 70 is drawn into the lumen of the handle 80. As the handle 80 is moved with respect to the cartridge 70, the push rod 85 pushes the medical device 90 in the delivery catheter 14. The pitch of the threads 72 can be varied as desired in order to change the amount of relative axial movement that occurs between the cartridge 70 and the handle 80 with each revolution of the nut 74. In one embodiment, a pitch of 1 revolution=½ inch axial movement was found to provide sufficient control of the medical device without requiring the physician to make too many rotations of the nut 74 in order to advance or retract it. Other thread pitches may include 1 revolution=¼, ⅜, ⅝ or ¾ inch axial movement.

In use, the physician routes the delivery catheter 14 to the desired location in the patient's body using any desired routing technique. With the distal end of the cartridge 70 engaged with the connector 30 at the end of the delivery catheter 14, the handle 80 can be advanced such that the push rod 85 forces the medical device 90 into and along the length of the delivery catheter 14. The fitting 82 on the distal end of the handle 80 then engages the leaves 76 of the nut 74, whereupon rotation of the nut 74 draws the cartridge 70 into the handle portion 80 (or draws the handle over the cartridge depending on whether the position of the handle or cartridge is fixed). Because the push rod 85 is fixed to the handle 80, rotating the nut 74 selectively moves the delivery catheter 14 with respect to the medical device 90 such that the medical device can be advanced or retracted from the distal end of the delivery catheter 14.

In order to prevent the physician from inadvertently advancing the medical device too far out of the distal end of the delivery catheter 14, one or more mechanisms may be provided to limit movement of the medical device 90 with respect to the delivery catheter 14. In one embodiment of the invention, one or more safety keys 104 can be fitted over the threads 72 on the cartridge. The safety keys 104 prevent the nut 74 from moving past the key 104 until the physician pulls the key off the cartridge. Each key can be color coded or contain printed reminders that instruct the physician to perform a desired procedure step prior to removal of the key. Once the key 104 is removed, the nut 74 can be advanced over the remainder of the cartridge 70 and thereby further advancing the medical device 90 out the distal end of the delivery catheter 14. Other safety mechanisms may include a source of friction on the threads 72 such that a threshold torque is required to move the nut 74 over the high friction threads. High friction threads are placed at locations where certain procedural steps are required to be completed. The high friction can be created with an o-ring, surface treatment, a spring or the like.

In one embodiment of the invention, the proximal end of the handle 80 includes a rotatable cap 110. The cap 110 is threaded such that upon rotation, a release wire is activated to disengage the medical device from the distal end of the push rod 85 and deploy it in the patient.

Figure 4:
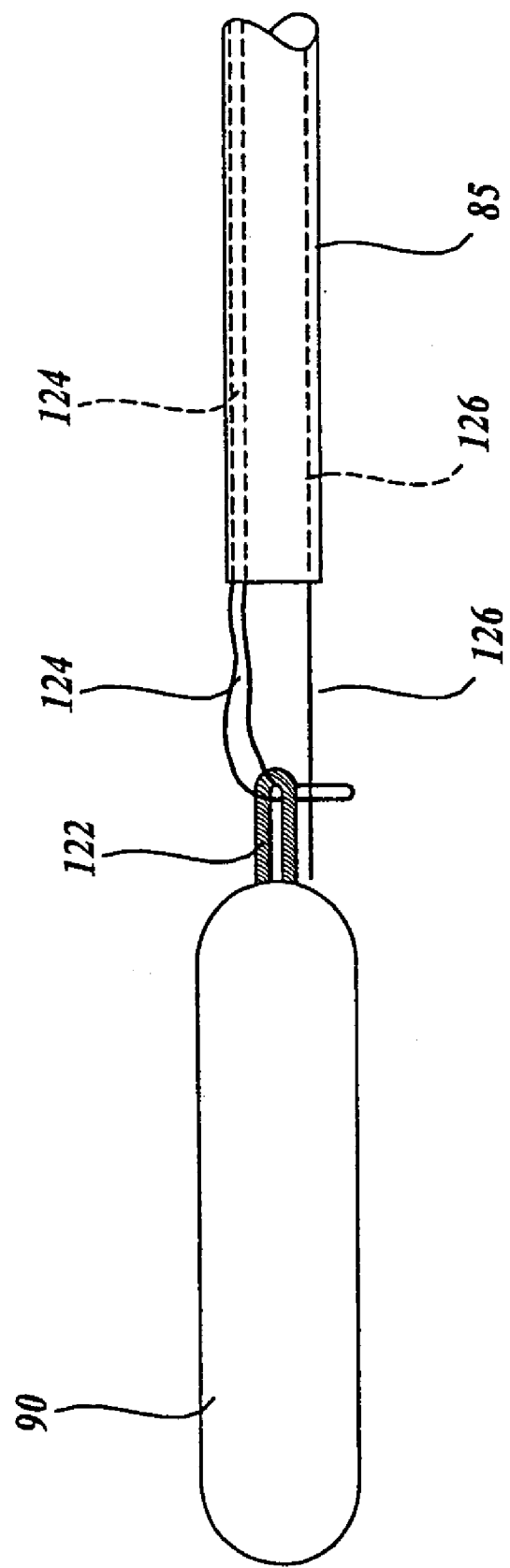
FIG. 4 illustrates one mechanism for releasably securing a medical device to a medical device delivery system.

FIG. 4 illustrates one embodiment of a mechanism for selectively releasing a medical device 90 from the distal end of the push rod 85 secured within the handle portion of the delivery system. In this embodiment, the medical device 90 includes an eyelet 122 through which a threaded loop 124 is passed. The threaded loop 124 is preferably made of a braided nylon or other high strength, low stretch material. A release wire 126 is also passed through the threaded loop 124 on the opposite side of the eyelet 122 such that the threaded loop 124 and the release wire 126 form a hitch over the eyelet 122. Upon retraction of the release wire 126, the threaded loop 124 is easily pulled out of the eyelet 122 and the medical device 90 can be disengaged from the push rod 85. In the embodiment shown, the push rod 85 is a hollow tube such that the thread that forms the threaded loop 124 and release wire 126 can be routed through a lumen of the push rod 85.

Figure 5:
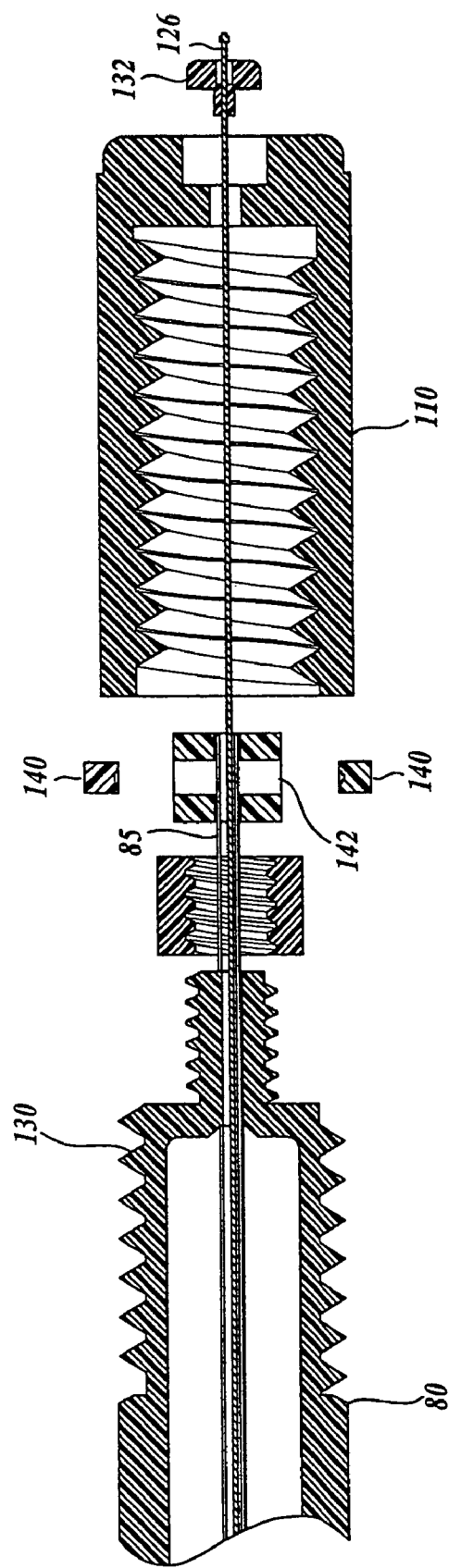
FIG. 5 illustrates an end cap at the proximal end of a handle.

FIG. 5 illustrates the end cap 110 at the proximal end of the handle 80. The end cap 110 is secured to the handle 80 by a set of threads 130 or other means. A button 132 at the proximal end of the end cap 110 is secured to the proximal end of the release wire 126 such that as the end cap 110 is rotated proximally on the threads 130, the release wire is also pulled proximally thereby releasing the medical device. The push rod 85 is secured to the handle 80 with a pair of set screws 140 in a bushing 142. The threads that form the loop 124 can also be tied off, soldered, crimped or threaded together at the bushing 142.

The push rod 85 is preferably formed of a hypotube at its proximal end and a wound coil at its distal end that are joined with a coupler. The wound coil provides sufficient flexibility so that the push rod 85 can be advanced on a tortuous path in the body. A polymer jacket may cover both the hypotube and the wound coil. Although a hypotube and wound coil make the preferred push rod, a polymer extruded tube or graphite shaft could also be used. Furthermore a solid rod could be used and the threads for the threaded loop and release wire routed adjacent the push rod.

Furthermore, the push rod could be a laser cut tubing with hydrophilic or Teflon® linings or coatings to provide sufficient lubricity of the push rod within the delivery catheter or an internal coating, for the threaded loop or release wire routed through the push rod.

In addition, each of these tubings may be reinforced with polymers, glass, ceramics, Teflon®, nylons, urethanes, polyethylenes, and polyolyfins, and combinations thereof. The catheter may have a variable durometer jacket extending along its length such that the distal tip may be more or less stiff than the proximal end of the catheter. Hydrophilic liner coatings may be provided to provide sufficient lubricity.

The delivery catheter 14 can be routed to a desired position in the body with a guide wire made from either stainless steel, Nitinol, graded fiber or combinations thereof. Alternatively, a dilator catheter could be used to route the catheter into its intended location. Such a dilator can be wire enforced, braid enforced, with a variable durometer sections as with the delivery catheter itself. Finally, a steering catheter could be used to route the delivery catheter 14 to its intended location. Such a steering catheter could include a one-way flex control, two-way flex control, and could be made of any materials used to manufacture the delivery catheter.

The medical device 90 may be a sent, vascular filter, time release drug delivery system or other device designed to be temporarily or permanently placed in a patient. In one actual embodiment of the invention, the medical device 120 is a suspension wire to be placed in the coronary sinus and great cardiac vein in order to aid in the closure of a mitral valve in the heart. Such a suspension wire is disclosed in U.S. patent application Ser. No. 10/011,867, titled "Anchor and Pull Mitral Valve Device and Method" filed Dec. 15, 2001, and Ser. No. 10/066,426, titled "Fixed Length Anchor and Pull Mitral Valve Device and Method" filed Jan. 30, 2002, which are herein incorporated by reference.

As can be seen, the present invention provides a mechanism for routing a medical device to a catheter does not limit the particular selection of delivery catheter or the method of placing it at the desired location. Any type of delivery catheter can be used provided it can be engaged with the cartridge that holds the medical device. Furthermore, because the medical device is pre-loaded in the cartridge, there is less likelihood that the medical device will become damaged as the physician inserts the medical device into the catheter.

While the preferred embodiment of the invention has been illustrated and described, it will be appreciated that various changes can be made therein without departing from the spirit and scope of the invention. Therefore the scope of the invention is to be determined from the following claims and equivalents thereof.

The embodiments of the invention in which an exclusive property or privilege is claimed are defined as follows:

1. A system for selectively advancing a medical device into a patient, comprising: a delivery catheter having a distal end that is inserted into a patient's body, a proximal end that remains outside the patient's body and one or more lumens that extend between the proximal and distal end; a cartridge that is engageable with the proximal end of the delivery catheter, the cartridge including a lumen that aligns with a lumen in the delivery catheter when the cartridge is engaged with the proximal end of the delivery catheter; a medical device positioned within the lumen of the cartridge; and an advancing mechanism for advancing the medical device out of the cartridge and into a lumen of the delivery catheter.

2. The system of claim 1, wherein the advancing mechanism comprises a push rod that engages the medical device.

3. The system of claim 2, wherein the proximal end of the push rod is secured to a handle.

4. The system of claim 3, wherein the handle and cartridge can be selectively engaged.

5. The system of claim 4, wherein the handle and cartridge are selectively engaged with a set of threads and a nut.

6. The system of claim 4, further comprising one or more devices for prohibiting the engagement of the handle and cartridge.

7. The system of claim 6, wherein the one or more devices for prohibiting the engagement of the handle and cartridge comprises a slot having at least one stop, and a tab that fits within the slot and engages the stop.

8. The system of claim 6, wherein the one or more devices for prohibiting the engagement of the handle and cartridge comprises a key that is engaged with one of the cartridge or handle to prevent relative motion between the handle and the cartridge.

9. A system for delivery a medical device to a desired location in a patient, comprising: a cartridge having a proximal end, a distal end and a cavity therein; a connector on the cartridge that engages a corresponding connector on a proximal end of a delivery catheter in order to align the cavity with a lumen of the delivery catheter; a medical device collapsed within the cavity; a push rod that engages a medical device and advances it into the lumen of the delivery catheter; a handle secured to the push rod; and means for selectively moving the handle and the cartridge including means for limiting the movement of the cartridge with respect to the handle.

10. The system of claim 9, wherein the push rod comprises a hypotube at a proximal end, a coil at the distal end and a coupler that joins the hypotube and coil.

11. The system of claim 10, further comprising a polymer jacket over the push rod.

12. The system of claim 9, wherein the cavity in the cartridge is tapered.

13. The system of claim 12, wherein the taper narrows distally in the cartridge.

14. The system of claim 12, wherein the taper narrows proximally in the cartridge.

15. The system of claim 9, wherein the medical device is compressed within the cartridge.

16. The system of claim 15, wherein the medical device is a self expanding stent.

17. The system of claim 15, wherein the medical device is a mitral valve suspension cable.

18. A method of deploying a medical device in a patient's body, comprising the acts of: advancing a distal end of a delivery catheter to a desired location in a patient's body; engaging a cartridge having a pre-loaded medical device therein to a proximal end of the delivery catheter; advancing the medical device out of the cartridge through a lumen of the delivery catheter to a distal end of the delivery catheter.

19. The method of claim 18, further comprising the act of: moving the delivery catheter with respect to the medical device such that the medical device is expelled from the distal end of the delivery catheter.

20. The method of claim 19, further comprising releasing a tether on the medical device so that it remains in the patient's body after removal of the delivery catheter.

21. The system of claim 1 wherein said medical device is adapted to be contained completely within said cartridge.

22. The system of claim 1 wherein said proximal end of said delivery catheter comprises a cartridge alignment element adapted to engage with said cartridge.

* * * * *